United States Patent [19]

Mohrs et al.

[11] Patent Number: 5,292,769
[45] Date of Patent: Mar. 8, 1994

[54] SUBSTITUTED MANDELIC ACID DERIVATIVES AND THEIR USE IN MEDICAMENTS

[75] Inventors: Klaus-Helmut Mohrs, Wuppertal; Siegfried Raddatz, Cologne; Michael Matzke, Wuppertal; Romanis Fruchtmann, Cologne; Armin Hatzelmann, Konstanz; Christian Kohlsdorfer, Erftstadt; Reiner Müller-Peddinghaus, Bergisch-Gladbach; Pia Theisen-Popp, Aachen, all of Fed. Rep. of Germany

[73] Assignee: Bayer Aktiengesellschaft, Leverkusen, Fed. Rep. of Germany

[21] Appl. No.: 934,059

[22] Filed: Aug. 21, 1992

[30] Foreign Application Priority Data

Aug. 29, 1991 [DE] Fed. Rep. of Germany ....... 4128681

[51] Int. Cl.$^5$ .................. C07D 215/16; A61K 31/47
[52] U.S. Cl. .................................... 514/311; 546/123
[58] Field of Search ......................... 546/173; 514/311

[56] References Cited

U.S. PATENT DOCUMENTS 4,952,695 8/1990 Groche et al. ................. 546/152

FOREIGN PATENT DOCUMENTS 0414078 8/1990 European Pat. Off. .

OTHER PUBLICATIONS

Jerry March, *Advanced Organic Chemistry*, pp. 837–840, (1977).
Houbey-Weyl, *Methoden der organischen Chemie*, (1973), pp. 289–302.
Uhlmann XII, pp. 367–375, (1976).
R. I. Trust, *Organic Synthesis*, 1973, pp. 116–122.
O. Grummitt, *Org. Synth. Coll.*, vol. IV, 1963, pp. 771–775.
H. Adkins, *Org. Synth. Coll.*, vol. II, 1943, pp. 606–608.
Gunter E. Jeromin, *Chem. Ber.*, 1987, pp. 649–650.
Pierre Borgeat, *Proc. Natl. Acad. Sci USA*, May 1979, pp. 2148–2152.

*Primary Examiner*—David B. Springer
*Attorney, Agent, or Firm*—Sprung Horn Kramer & Woods

[57] ABSTRACT

Substituted mandelic acid derivatives can be prepared by reaction of glyoxylic esters with Grignard compounds. The substituted mandelic acid derivatives are suitable as active compounds in medicaments, in particular for medicaments which inhibit leukotriene synthesis.

10 Claims, No Drawings

SUBSTITUTED MANDELIC ACID DERIVATIVES AND THEIR USE IN MEDICAMENTS

The invention relates to substituted mandelic acid derivatives, processes for their preparation and their use in medicaments.

It is already known that 4-(quinolin-2-yl-methoxy)-phenylacetic acid derivatives and a-substituted 4-(quinolin-2yl-methoxy)phenylacetic acid derivatives have a lipoxygenase-inhibiting action [compare EP 344,519 (U.S. Pat. No. 4,970,215) and EP 339,416].

The present invention relates to substituted mandelic acid derivatives of the general formula (i)

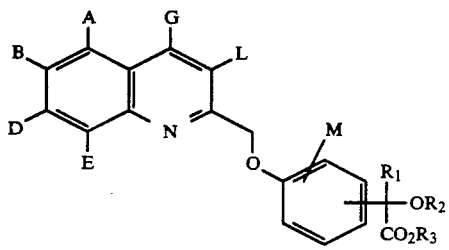

in which
A, B, D, Et Go, L and M are identical or different and represent hydrogen, hydroxyl, halogen, trifluoromethyl, trifluoromethoxy or carboxyl, represent straight-chain or branched alkyl which has up to 10 carbon atoms and is optionally substituted by hydroxyl or halogen, represent straight-chain or branched alkoxy or alkoxycarbonyl having up to 10 carbon atoms or represent aryl which has 6 to 10 carbon atoms and is optionally substituted by halogen, nitro, cyano or by straight-chain or branched alkyl or alkoxy having in each case up to 8 carbon atoms,
$R^1$ represents a group of the formula

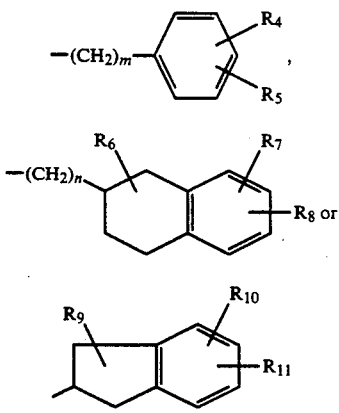

wherein
n and m are identical or different and denote the number 1, 2, 3, 4, 5, 6, 7 or 8 and
$R^4$, $R^5$, $R^6$, $R^7$, $R^8$, $R^9$, $R^{10}$ and $R^{11}$ are identical or different and denote hydrogen, halogen, nitro, cyano, hydroxyl, carboxyl, trifluoromethyl, trifluoromethoxy or straight-chain or branched alkyl, alkoxy or alkoxycarbonyl having in each case up to 8 carbon atoms,
$R^2$ represents hydrogen or represents straight-chain or branched alkyl having up to 8 carbon atoms, and
$R^3$ represents hydrogen or straight-chain or branched alkyl having up to 8 carbon atoms,
and salts thereof.

Physiologically acceptable salts are preferred in the context of the present invention. Physiologically acceptable salts of the substituted mandelic acid derivatives can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention are furthermore metal salts, preferably of monovalent metals, and the ammonium salts. Alkali metal salts, such as, for example, sodium and potassium salts, and ammonium salts are preferred.

The compounds according to the invention exist in stereoisomeric forms which either behave as mirror images (enantiomers) or do not behave as mirror images (diastereomers). The invention relates both to the antipodes and to the racemic forms, as well as to the diastereomeric mixtures. Like the diastereomers, the racemic forms can be separated into the stereoisomerically uniform constituents in a known manner [compare E. L. Eliel, Stereochemistry of Carbon Compounds, McGraw Hill, 1962].

Preferred compounds of the general formula (I) are those in which
A, B, D, E, G, L and M are identical or different and represent hydrogen, fluorine, chlorine, bromine, trifluoromethoxy or carboxyl, represent straight-chain or branched alkyl which has up to 8 carbon atoms and is optionally substituted by hydroxyl, fluorine, chlorine or bromine, represent straight-chain or branched alkoxy or alkoxycarbonyl having in each case up to 8 carbon atoms or represent phenyl which is optionally substituted by fluorine, chlorine, bromine, nitro, cyano or by straight-chain or branched alkyl or alkoxy having in each case up to 6 carbon atoms,
$R^1$ represents a group of the formula

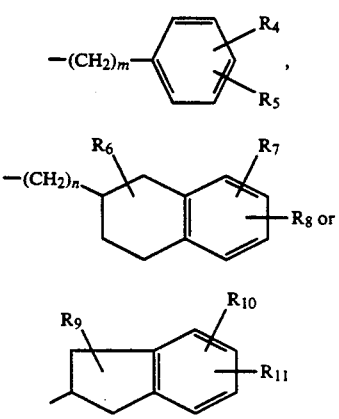

wherein n and m are identical or different and denote the number 1, 2, 3, 4, 5, 6 or 7 and $R^4$, $R^5$, $R^6$, $R^7$, $R^8$, $R^9$, $R^{10}$ and $R^{11}$ are identical or different and denote hydrogen, fluorine, chlorine, bromine, trifluoromethyl, trifluoromethoxy or straight-chain or branched alkyl or alkoxy having in each case up to 6 carbon atoms, $R^2$ represents hydrogen or straight-chain or branched alkyl having up to 6 carbon atoms and $R^3$ represents hydrogen or straight-chain or branched alkyl having up to 6 carbon atoms, and salts thereof.

Particularly preferred compounds of the general formula (I) are those in which

A, B, D, E, G, L and M are identical or different and represent hydrogen, fluorine, chlorine or straight-chain or branched alkyl or alkoxy having in each case up to 6 carbon atoms, $R^1$ represents a group of the formula

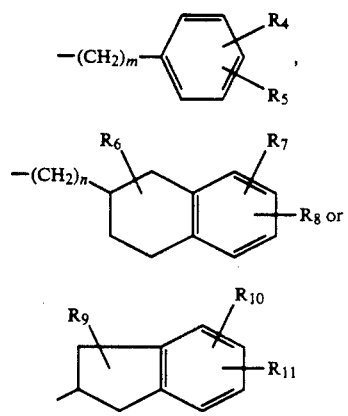

wherein n and m are identical or different and denote the number 1, 2, 3, 4, 5 or 6 and $R^4$, $R^5$, $R^6$, $R^7$, $R^8$, $R^9$, $R^{10}$ and $R^{11}$ are identical or different and denote hydrogen, fluorine, chlorine, bromine, trifluoromethyl, trifluoromethoxy or straight-chain or branched alkyl or alkoxy having in each case up to 4 carbon atoms, $R^2$ represents hydrogen or straight-chain or branched alkyl having up to 4 carbon atoms and $R^3$ represents hydrogen or straight-chain or branched alkyl having up to 4 carbon atoms, and salts thereof.

Especially preferred compounds of the general formula (I) are those in which

A, B, D, E, G, L and M represent hydrogen. Those compounds in which the radical of the formula $-C(R^1)(OR^2)(CO_2R^3)$ is in the 4-position relative to the quinolylmethoxy radical are furthermore particularly preferred.

A process for the preparation of the compounds of the general formula (I) according to the invention has furthermore been found and is characterised in that glyoxylic esters of the general formula (II)

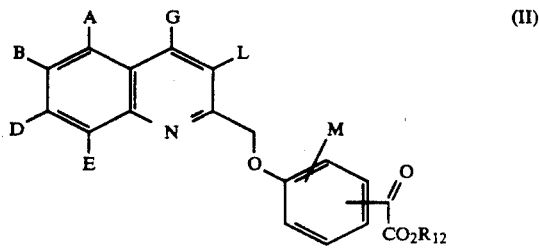

in which

A, B, D, E, G, L and M have the abovementioned meaning and $R^{12}$ has the abovementioned meaning of $R^3$, but does not represent hydrogen, are reduced with Grignard or organometallic compounds of the general formula (III)

$$R^1-V \qquad (III)$$

in which $R^1$ has the abovementioned meaning and

V represents the typical Grignard radical W—Z, wherein

W denotes magnesium, cadmium or zinc, and

Z denotes chlorine, bromine or iodine, or represents lithium, sodium, magnesium, aluminium, cadmium or zinc, in inert solvents, the group V being split off, and in the case where $R^2$ does not represent hydrogen, the products are etherified by the customary method, and in the case of the acids ($R^3$=H), the esters are hydrolysed, and in the case of the enantiomers, the corresponding enantiomerically pure acids ($R^3$=H) are separated, it being possible for the substituents A, B, D, E, G, L and M to be varied by customary methods, if appropriate.

The process according to the invention can be illustrated by an equation by way of example:

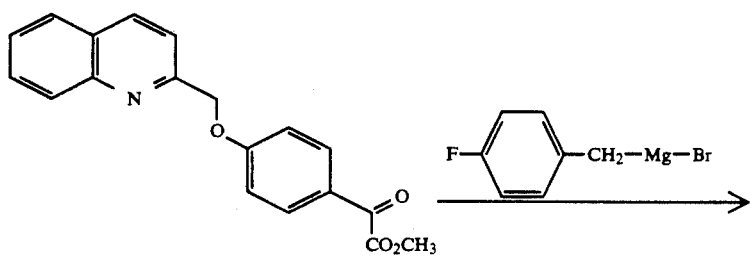

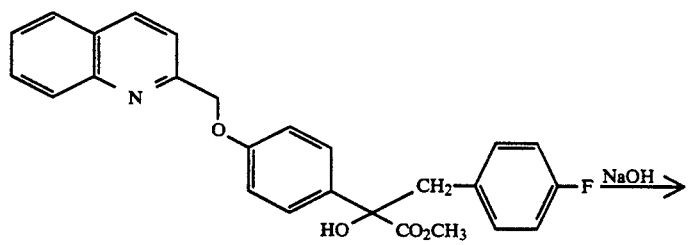

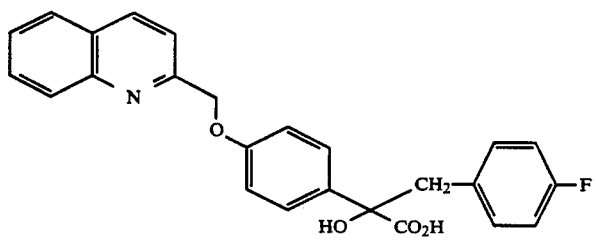

Suitable solvents for the reduction are the customary organic solvents which do not change under the reaction conditions. These include, preferably, ethers, such as diethyl ether, dioxane, tetrahydrofuran and glycol dimethyl ether, or hydrocarbons, such as benzene, toluene, xylene, hexane and cyclohexane, or petroleum fractions or dimethylformamide. It is also possible to use mixtures of the solvents mentioned. Tetrahydrofuran and diethyl ether are preferred.

The reduction is in general carried out in a temperature range from −80° C. to +30° C., preferably at −40° C. to +25° C.

The reduction is in general carried out under normal pressure. However, it is also possible to carry out the process under increased pressure or under reduced pressure (for example in a range from 0.5 to 5 bar).

The group V is split off by the method customary for Grignard reactions, using aqueous ammonium chloride solution [compare J. March, Advanced organic Chemistry, Second Edition page 836].

The compounds of the general formula (III) are known per se or can be prepared by the customary method [compare K. Nützel, Houben-Weyl, Methoden der organischen Chemie (methods of Organic Chemistry), 4th Edition volume 13/2a, 53 et seq. (Themie Verlag, Stuttgart) 1973; X.S. Kharash, O. Reinmuth, Grignard Reactions of Nonmetallic Compounds, Prentice Hall, New York, 1974; Uhlman XII, 370; Houben-Weyl XIII/2a, 289-302; R.I. Trust, R.E. Ireland, Org. Synth. 53 116, (1973); O. Grummitt, E.I. Becker, Org. Synth. Coll. Volume IV, 771 (1963); and H. Adkins, W. Zartman, Org. Synth. Coll. Volume II, 606 (1943)].

1 to 3 mol, preferably 1.1 mol, of the Grignard compounds or of the organometallic compounds of the general formulae (III) are in general employed per mol of the glyoxylic esters of the general formula (II).

The compounds of the general formula (II) are known per se [compare EP 414,078] and and can be prepared, for example, by etherifying compounds of the general formula (IV)

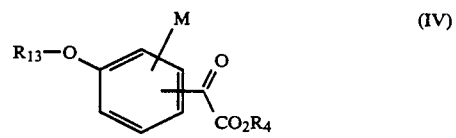

in which $R^4$ and M have the abovementioned meaning and $R^{13}$ represents a typical hydroxyl-protective group, such as, for example, benzyl or tert-butyl, with halogenomethylquinolines of the formula (V)

(V)

[Structure V with substituents A, B, D, E, G, L and $CH_2-R_{14}$]

in which

A, B, D, E, G and L have the abovementioned meaning and $R^{14}$ represents halogen, preferably chlorine or bromine, if appropriate in the presence of a base, after the protective group $R^{13}$ has been split off in inert solvents.

The protective groups are split off from the corresponding ethers by the customary methods, for example by hydrogenolytic cleavage of the benzyl ethers in the abovementioned inert solvents in the presence of a catalyst using hydrogen gas [compare also Th. Greene: "Protective Groups in organic Synthesis", J. Wiley/Sons, 81, New York].

The etherification can be carried out in inert organic solvents, if appropriate in the presence of a base.

Solvents for the etherification can be inert organic solvents which do not change under the reaction conditions. These include, preferably, ethers, such as, for example, dioxane, tetrahydrofuran or diethyl ether, halogenohydrocarbons, such as methylene chloride, chloroform, carbon tetrachloride, 1,2-dichloroethane or trichloroethylene, hydrocarbons, such as benzene, xylene, toluene, hexane or cyclohexane, or petroleum fractions, nitromethane, dimethylformamide, acetonitrile, acetone or hexamethylphosphoric acid triamide. It is also possible to employ mixtures of the solvents.

Inorganic or organic bases can be employed as bases for the etherification. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or organic amines (trialkyl ($C_1$-$C_6$) amines), such as triethylamine, or heterocyclic compounds, such as pyridine, methylpiperidine, piperidine or morpholine.

It is also possible to employ alkali metals, such as sodium, and hydrides thereof, such as sodium hydride, as bases.

The etherification is in general carried out in a temperature range from 0° C. to +150° C., preferably from +10° C. to +100° C.

The etherification is in general carried out under normal pressure. However, it is also possible to carry out the process under reduced pressure or increased pressure (for example in a range from 0.5 to 5 bar).

0.5 to 5, preferably 1 to 2 mol, of halide are in general employed per mol of the reaction partner. The base is in general employed in an amount of 0.5 to 5 mol, preferably 1 to 3 mol, based on the halide.

The compounds of the general formula (IV) are known or can be prepared by the customary method [compare Chem. Commun. 1972, (11), 668].

The compounds of the general formula (V) are also known or can be prepared by the customary method [compare Chem. Ber. 120, 649 (1987)].

The carboxylic acid esters are hydrolysed by customary methods by treating the esters with customary bases in inert solvents.

Suitable bases for the hydrolysis are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate, or sodium bicarbonate. Sodium hydroxide or potassium hydroxide is particularly preferably employed.

Suitable solvents for the hydrolysis are water or the organic solvents customary for a hydrolysis. These include, preferably, alcohols, such as methanol, ethanol, propanol, isopropanol or butanol, or ethers, such as tetrahydrofuran or dioxane, or dimethylformamide or dimethylsulphoxide. Alcohols, such as methanol, ethanol, propanol or isopropanol, are particularly preferably used. It is also possible to employ mixtures of the solvents mentioned.

The hydrolysis is in general carried out in a temperature range from 0° C. to +100° C., preferably from +20° C. to +80° C.

The hydrolysis is in general carried out under normal pressure. However, it is also possible to carry out the hydrolysis under reduced pressure or under increased pressure (for example from 0.5 to 5 bar).

In carrying out the hydrolysis, the base is in general employed in an amount of 1 to 3 mol, preferably 1 to 1.5 mol, per mol of the ester. Molar amounts of the reactants are particularly preferably used.

The compounds of the general formula (1) surprisingly exhibit a high activity as inhibitors of leukotriene synthesis, especially after oral administration.

The substituted mandelic acid derivatives according to the invention can be employed as active compounds in medicaments. The substances can act as inhibitors of enzymatic reactions in the context of arachidonic acid metabolism, in particular of 5-lipoxygenase.

They are therefore preferably suitable for the treatment and prevention of diseases of the respiratory passages, such as allergies/asthma, bronchitis, emphysema, shock lung, pulmonary hypertension, inflammations/rheumatism and oedemas, thromboses and thromboembolisms, ischaemias (disturbances in peripheral, cardiac or cerebral circulation), cardiac and cerebral infarctions, disturbances in cardiac rhythm, angina pectoris and arteriosclerosis, in the event of tissue transplants, dermatoses, such as psoriasis, inflammatory dermatoses, for example eczema, dermatophyte infection, infections of the skin by bacteria, metastases and for cytoprotection in the gastrointestinal tract.

The substituted mandelic acid derivatives according to the invention can be used both in human medicine and in veterinary medicine.

The pharmacological action data of the substances according to the invention are determined by the following method:

The release of leukotriene $B_4$ ($LTB_4$) by polymorphonuclear human leucocytes (PMN) after addition of the substances and Ca ionophore was determined was means of reverse phase HPLC by the method of Borgeat, P. et al., Proc. Nat. Acad. Sci. 76, 2148-2152 (1979), as a measure of the 5-lipoxygenase inhibition.

The present invention also includes pharmaceutical formulations which contain one or more compounds of the general formula (I), in addition to inert, non-toxic, pharmaceutically suitable auxiliaries and excipients, or which consist of one or more active compounds of the formula (I), and to processes for the preparation of these formulations.

The active compounds of the formula (I) should be present in these formulations in a concentration of 0.1 to 99.5% by weight, preferably 0.5 to 95% by weight of the total mixture.

The pharmaceutical formulations can also contain other pharmaceutical active compounds, in addition to the active compounds of the formula (I).

The abovementioned pharmaceutical formulations can be prepared in the customary manner by known methods, for example using the auxiliary or excipient substance or substances.

In general, it has proved advantageous to adminster the active compound or compounds of the formula (I) in total amounts of about 0.01 to about 100 mg/kg, preferably in total amounts of about 1 mg/kg to 50 mg/kg of body weight every 24 hours, if appropriate in the form of several individual doses, in order to achieve the desired result.

However, it may be advantageous to deviate from the amounts mentioned, and in particular to do so as a function of the nature and body weight of the subject treated, of the individual behaviour towards the medicament, of the nature and severity of the disease, of the nature of the formulation and administration, and of the time or interval at which administration takes place.

PREPARATION EXAMPLES

Example 1

Methyl 2-[4-quinolin-2-yl-methoxy)phenyl]-3-(4-fluorophenyl)-2-hydroxy-propionate

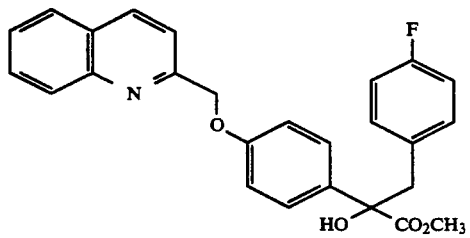

A freshly prepared Grignard solution of 4.86 g (0.0257 mol) of 4-fluorobenzyl bromide and 0.625 g (0.0257 mol) of magnesium filings in 50 ml of diethyl ether is slowly added dropwise to a solution of 5 g (0.0158 mol) of methyl 4-(quinolin-2-yl-methoxy)-phenylglyoxylate (preparation: Mohrs et al., EP 414,078, A2) in 50 ml of tetrahydrofuran at 0° C. under an inert gas and with exclusion of moisture. After the reaction mixture has been heated to 25° C., it is poured onto ice-water, acidified with ammonium chloride and extracted twice with ethyl acetate, the organic phases are dried over sodium sulphate and evaporated and the residue is chromatographed on silica gel 60 (cyclohexane/ethyl acetate 3:1).

Yield: 2.17 g (31.8% of theory)
Melting point: 155° C. (H₃COH)

The compounds listed in Table 1 are prepared analogously to Example 1:

TABLE 1

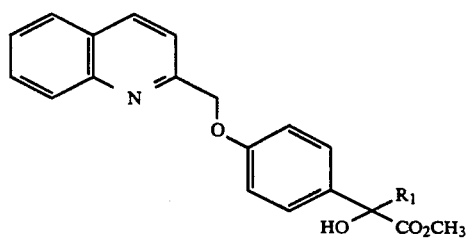

| Ex. No. | R¹ | Melting point: | Yield |
|---|---|---|---|
| 2 | —CH₂—(3-CF₃-phenyl) | 89° C. | 48.6% |
| 3 | —CH₂—(3-OCH₃-phenyl) | —a) | 83% |
| 4 | —(CH₂)₂—(4-F-phenyl) | —a) | 30.5% |
| 5 | —(CH₂)₂—phenyl | —a) | 32.2% |
| 6 | —(CH₂)₂—(4-OCH₃-phenyl) | —a) | 30.4% |
| 7 | —(CH₂)₃—phenyl | —a) | 43.3% |
| 8 | —(CH₂)₄—phenyl | —a) | 37.5% |
| 9 | —(CH₂)₅—phenyl | —a) | 40.0% |
| 10 | —CH₂—phenyl | 161° C. | 23.0% |
| 11 | indanyl | 132° C. | 30.7% |
| 12 | —CH₂—tetrahydronaphthyl | —a) | 36.5% | a)The compounds are immediately reacted further after chromatography

Example 13

2-[4-(Quinolin-2-yl-methoxy)phenyl]-3-(4-fluorophenyl)-2-hydroxy-propionic acid

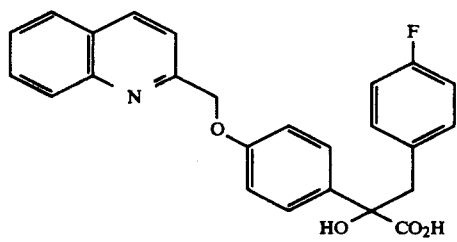

2.1 g (48.7 mmol) of the compound from Example 1 are heated under reflux in 50 ml of methanol and 5 ml of 2 N sodium hydroxide solution for 15 hours. After cooling, the mixture is neutralised with 5 ml of 2 N hydrochloric acid and the product which has precipitated is filtered off with suction and recrystallised from methanol.
Yield: 1.86 g (91.6% of theory)
Melting point: 203° C. (H₃COH)

The derivatives shown in Table 2 are prepared analogously to Example 13:

TABLE 2

| Ex. No. | R¹ | Melting point:[b] | Yield |
|---|---|---|---|
| 14 | —CH₂—(3-CF₃-phenyl) | 204° C. | 57% |
| 15 | —CH₂—(3-OCH₃-phenyl) | 228° C. | 78.5% |
| 16 | —(CH₂)₂—(4-F-phenyl) | 168° C. | 51% |
| 17 | —(CH₂)₂—phenyl | 178° C. | 67% |
| 18 | —(CH₂)₂—(4-OCH₃-phenyl) | 182° C. | 67.7% |

TABLE 2-continued

| Ex. No. | R¹ | Melting point:[b] | Yield |
|---|---|---|---|
| 19 | —(CH₂)₃—phenyl | 194° C. | 61% |
| 20 | —(CH₂)₄—phenyl | 147° C. | 73.7% |
| 21 | —(CH₂)₅—phenyl | 141° C. | 52% |
| 22 | —CH₂—phenyl | 200° C. | 74.5% |
| 23 | —(2-indanyl) | 208° C. | 68.5% |
| 24 | —CH₂—(tetrahydronaphthyl) | 194° C. | 88.2% |

[b] recrystallised from methanol

Examples 25 and 26

(+)-2-[4-Quinolin-2-yl-methoxy)phenyl]-2-(2-indanyl)-2-hydroxyacetic acid (25)

(−)-[4-Quinolin-2-yl-methoxy)phenyl]-2-(2-indanyl)-2-hydroxyacetic acid (26)

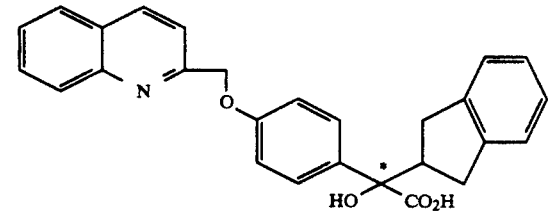

5 g of the racemate from Example 23 were separated preparatively on chiral phases under standard conditions. Yield in each case 2 g of the enantiomerically pure compounds.

| (+) Enantiomer: | ee > 99 (HPLC) |
|---|---|

| | |
|---|---|
| (25) | $\alpha_D^{20}$ + 18.5 (c = 1, MeOH) |
| | Melting point: 181° C. (MeOH) |
| (−) Enantiomer: | ee > 99 (HPLC) |
| (26) | $\alpha_D^{20}$ − 18.8 (c = 1, MeOH) |
| | Melting point: 181° C. (MeOH) |

We claim:

1. A substituted mandelic acid derivative compound of the formula:

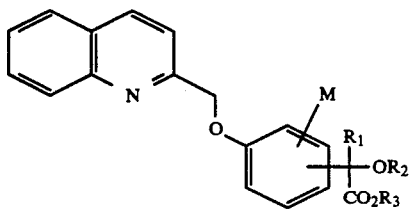

wherein

M represents hydrogen, fluorine, chlorine, bromine, trifluoromethoxy or carboxyl; or represents straight-chain or branched alkyl which has up to 8 carbon atoms and is optionally substituted by hydroxyl, fluorine, chlorine or bromine; or represents straight-chain or branched alkoxy or alkoxycarbonyl having in each case up to 8 carbon atoms; or represents phenyl which is optionally substituted by fluorine, chlorine, bromine, nitro, cyano or by straight-chain or branched alkyl or alkoxy having in each case up to 6 carbon atoms;

$R_1$ represents a group of the formula:

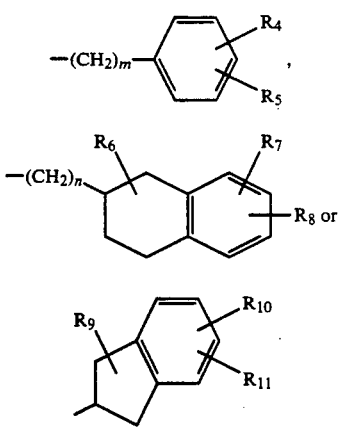

wherein n and m are identical or different and denote the number 1, 2, 3, 4, 5, 6 or 7; and $R_4$, $R_5$, $R_6$, $R_7$, $R_8$, $R_9$, $R_{10}$ and $R_{11}$ are identical or different and denote hydrogen, fluorine, chlorine, bromine, trifluoromethyl, trifluoromethoxy or straight-chain or branched alkyl or alkoxy having in each case up to 6 carbon atoms;

$R_2$ represents hydrogen or straight-chain or branched alkyl having up to 6 carbon atoms; and $R_3$ represents hydrogen or straight-chain or branched alkyl having up to 6 carbon atoms;

or a physiologically acceptable salt thereof.

2. A compound according to claim 1, wherein

M represents hydrogen, fluorine, chlorine or straight-chain or branched alkyl or alkoxy having in each case up to 6 carbon atoms;

n and m are identical or different and denote the number 1, 2, 3, 4, 5 or 6; and $R_4$, $R_5$, $R_6$, $R_7$, $R_8$, $R_9$, $R_{10}$ and $R_{11}$ are identical or different and denote hydrogen, fluorine, chlorine, bromine, trifluoromethyl, trifluoromethoxy or straight-chain or branched alkyl or alkoxy having in each case up to 4 carbon atoms;

$R_2$ represents hydrogen or straight-chain or branched alkyl having up to 4 carbon atoms; and $R_3$ represents hydrogen or straight-chain or branched alkyl having up to 4 carbon atoms; or a physiologically acceptable salt thereof.

3. A compound according to claim 1, wherein the radical of the formula —C($R^1$)(O$R^2$)CO$_3R^3$) is in the 4-position relative to the quinolylmethoxy radical.

4. A compound according to claim 1 wherein such compound is methyl-2-[4-(quinolin-2-yl-methoxy)-phenyl]-2-(2-indanyl)-2-hydroxy acetate of the formula

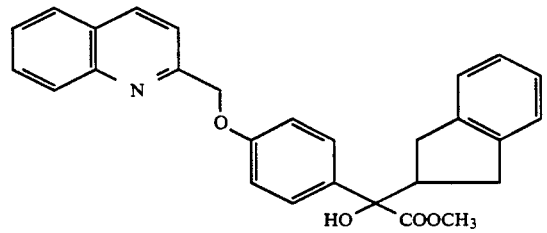

or a salt thereof.

5. A compound according to claim 1 wherein such compound is 2-[4-(quinolin-2-yl-methoxy)phenyl]-3-(3-trifluoromethyl-phenyl)-2-hydroxy-propionic acid of the formula

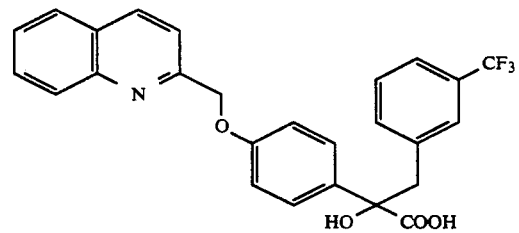

or a physiologically acceptable salt thereof.

6. A compound according to claim 1 wherein such compound is (')-2-[4-(quinolin-2-yl-methoxy)phenyl]-2-(2-indanyl)-2-hydroxy acetic acid of the formula

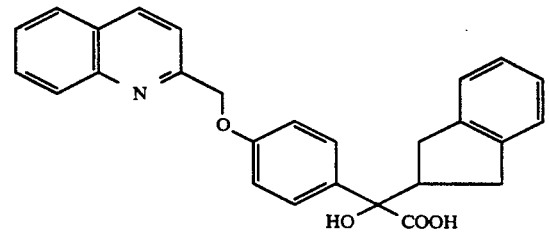

or a physiologically acceptable salt thereof.

7. A compound according to claim 1 wherein such compound is (+)-2-[4-(quinolin-2-yl-methoxy)phenyl]-2-(2-indanyl)-2-hydroxy acetic acid or a physiologically acceptable salt thereof.

8. A compound according to claim 1 wherein such compound is (−)-2-[4-(quinolin-2-yl-methoxy)phenyl]-2-(2-indanyl)-2-hydroxy acetic acid or a physiologically acceptable salt thereof.

9. A composition useful to inhibit leukotriene synthesis comprising an amount effective therefor of a compound or physiologically acceptable salt thereof according to claim 1 and a pharmacologically acceptable diluent.

10. A method of inhibiting leukotriene synthesis in a patient comprising administering to such patient an amount effective therefor of a compound or physiologically acceptable salt thereof according to claim 1.

* * * * *